United States Patent [19]

Rechner et al.

[11] Patent Number: 5,523,451
[45] Date of Patent: Jun. 4, 1996

[54] PROCESS FOR THE CONTINUOUS PREPARATION OF ARYL CARBONATES

[75] Inventors: Johann Rechner; Norbert Schön, both of Krefeld; Paul Wagner, Düsseldorf; Hans-Josef Buysch, Krefeld; Stephan Kabelac, Langenfeld, all of Germany

[73] Assignee: Bayer Aktiengesellschaft, Leverkusen, Germany

[21] Appl. No.: 206,575

[22] Filed: Mar. 4, 1994

[30] Foreign Application Priority Data

Mar. 12, 1993 [DE] Germany .......................... 43 07 852.4
May 17, 1993 [DE] Germany .......................... 43 16 428.5

[51] Int. Cl.$^6$ .................................................. C07C 69/96
[52] U.S. Cl. ................................... 558/270; 558/274
[58] Field of Search .................................. 558/274, 270

[56] References Cited

U.S. PATENT DOCUMENTS

| | | | |
|---|---|---|---|
| 4,410,464 | 10/1983 | Hallgren | 558/270 |
| 5,210,268 | 5/1993 | Fukuoka et al. | 558/270 |
| 5,362,901 | 11/1994 | Wagner et al. | 558/270 |

FOREIGN PATENT DOCUMENTS

| | | |
|---|---|---|
| 0461274 | 12/1991 | European Pat. Off. . |
| 3308921 | 9/1983 | Germany . |
| WO92/18458 | 10/1992 | WIPO . |

OTHER PUBLICATIONS

Patent Abstract of Japan, JP 4230242, Aug. 19, 1992 vol. 16, No. 581 (C–1012); Fukuoka Shinsuke, "Continuous Production of Diaryl Carbonate"; p. 1.

Patent Abstracts of Japan, JP 4235951, Aug. 25, 1992, vol. 16, No. 584 (C–1013) ; Fukuoka Shinsuke, "Continuous Production of Diaryl Carbonate"; p. 1.

*Primary Examiner*—José G. Dees
*Assistant Examiner*—Dwayne C. Jones
*Attorney, Agent, or Firm*—William C. Gerstenzang; Sprung Horn Kramer & Woods

[57] ABSTRACT

Organic carbonates which contain at least one aromatic ester group can be obtained continuously from carbonates, which contain at least one aliphatic ester group, and a phenolic compound in the presence of a transesterification catalyst known per se in that the reaction is carried out in a bubble column reactor or in a cascade of at least two bubble column reactors in such a way that the phenolic compound is metered into the first bubble column and the carbonate containing at least one aliphatic ester group is metered into each individual bubble column, but preferably only into the last bubble column. The carbonate containing at least one aromatic ester group is taken off in the liquid state from the last bubble column. Volatile reaction products, for example eliminated alcohol or a dialkyl carbonate are taken off at the upper end of each individual bubble column, preferably at the upper end of the first bubble column.

20 Claims, 3 Drawing Sheets

PROCESS FOR THE CONTINUOUS PREPARATION OF ARYL CARBONATES

BACKGROUND OF THE INVENTION

1. Field of the Invention

The invention relates to a continuous process for the preparation of aryl carbonates from carbonates containing at least one aliphatic ester group and phenols on the one hand and from alkyl aryl carbonates on the other hand by catalysed transesterification, the reaction being carried out in one or more bubble columns.

2. Description of the Related Art

The preparation of aromatic and aliphatic-aromatic carbonic esters (carbonates) by transesterification, starting from aliphatic carbonic esters and phenols, is known in principle. This is an equilibrium reaction, the position of the equilibrium being shifted almost completely in the direction of the aliphatically substituted carbonates. Therefore, it is relatively easy to prepare aliphatic carbonates from aromatic carbonates and alcohols. However, in order to carry out the reaction in the reverse direction towards aromatic carbonates, it is necessary to shift effectively the highly unfavourably lying equilibrium, not only highly active catalysts, but also a favourable procedure having to be used.

For the transesterification of aliphatic carbonic esters with phenols, a multiplicity of effective catalysts have been recommended, such as for example alkali metal hydroxides, Lewis acid catalysts selected from the group comprising the metal halides (German Offenlegungsschrift 2 528 412 and 2 552 907), organotin compounds (EP 0 000 879, EP 0 000 880, German Offenlegungsschrift 3 445 552, EP 0 338 760), lead compounds (JP 57/176 932), Lewis acid/proton acid catalysts (German Offenlegungsschrift 3 445 553).

In the known processes, the transesterification is carried out in a batchwise reactor at atmospheric pressure or under pressure, with or without an additional separation column. Even with the most highly active catalysts, reaction times of many hours are required in these cases to achieve even only average conversion rates of approximately 50% of phenol. Thus in the batchwise transesterification of phenol with diethyl carbonate at 180° C. using various organotin compounds, as described in German Offenlegungsschrift 3 445 552, yields of diphenyl carbonate of an order of magnitude of more than 20% are only achieved after a reaction time of approximately 24 hours; in the batchwise transesterification of phenol and dimethyl carbonate with the aid of organotin catalysts, as described in EP 0 000 879, the phenol conversion rate after 30 h is 34% of the theoretical value.

This means that, owing to the unfavourable thermodynamic conditions, the batchwise transesterification reactions described, even with the use of highly active catalyst systems, can only be carried out in the sense of an industrial process highly disadvantageously, since very poor space-time yields and high residence times with high reaction temperatures are required.

Such procedures are also particularly disadvantageous since even with highly selective transesterification catalysts at high temperatures and with long residence times of many hours, a marked proportion of side reactions occurs, for example ether formation with elimination of carbon dioxide.

It was therefore attempted to shift the reaction equilibrium as rapidly as possible in the direction of the products by adsorption to molecular sieves of the alcohol resulting in the transesterification (German Offenlegungsschrift 3 308 921). From the description of this procedure it appears that, for the adsorption of the reaction alcohol, a large amount of molecular sieve is required, which exceeds the amount of liberated alcohol by at least five fold. Furthermore, the molecular sieves used must be regenerated even after a short time and the conversion rate to the alkyl aryl carbonate intermediates is relatively low. This process therefore also appears not to be advantageously industrially and economically applicable.

A continuous transesterification process for the preparation of aromatic carbonates in which the reaction is carried out in one or more multiple-stage sequentially-connected distillation columns is described in EP-A 0 461 274. In this case, phenols are initially reacted with dialkyl carbonates to give aryl carbonate mixtures which in the main contain alkyl aryl carbonates. In a second, preferably downstream, multiple-stage distillation column, these are then further reacted to give the desired diaryl carbonate end products. The applicant emphasizes the effectiveness and the selectivity of its procedure.

Apart from conversion rates and selectivity, the citation of the space-time yield (STY) serves as a criterion for the evaluation of a process for those skilled in the art, since it describes the yield of product per unit of apparatus volume used. By way of the example of the transesterification of dimethyl carbonate (DMC) with phenol to give methyl phenyl carbonate (MPC) and diphenyl carbonate (DPC), the applicant of EP 0 461 274 shows a comparison of the batch mode of operation in an autoclave (Comparative Example 1) with a mode of operation in a multiple-stage distillation column (Example 1). In this case, only an increase of the STY from 5 to 8 g of the sum of DPC+MPC/l.h is achieved, as can easily be calculated from the examples. The STYs are comparatively low in both examples; only the MPC selectivity increased in the mode of operation in a multiple-stage distillation column from 94% to 97%. These results are achieved already under optimal conditions with the best transesterification catalysts at high temperatures and elevated pressure, so that further improvements do not appear to be possible.

The further reaction of the alkyl aryl carbonates to give diaryl carbonates proceeds in the procedure cited, as follows from the examples, in the sense of a disproportionation reaction. It is thus no wonder that in this reaction proceeding more readily in comparison to the first transesterification stage significantly higher STYs are achieved.

For the second transesterification stage, EP 0 461 274 compares the transesterification of methyl phenyl carbonate (MPC) to give diphenyl carbonate (DPC) in the batch mode of operation in the autoclave (Comparative Example 2) with carrying out the transesterification in a multiple-stage distillation column (Example 11). In this case, the STYs for DPC calculated from the data given there even show a reduction in the effectiveness from 144 g of DPC/l.h to 133 g of DPC/l.h. Only the formation of the by-product anisole occurs to a lesser extent.

Because of these figures and the considerably higher apparatus complexity, the improvement demonstrated here must be evaluated extremely sceptically.

The aim of an improvement of the transesterification reaction according to the invention should therefore primarily be an increase of the STYs, primarily of the transesterification stages with phenol, in which the selectivity of the overall process should not be reduced.

SUMMARY OF THE INVENTION

Surprisingly, it has now been found that the increase of the STYs succeeds in a continuously performed transesterification process at very high selectivity in bubble columns. This was particularly surprising, since bubble columns are putatively unsuitable reactors for this reaction, resemble batchwise reactors in their properties and in them, therefore, longer liquid residence times occur compared with a distillation column, which increase the risk of formation of by-products. High STYs in the carbonate transesterification according to the invention are accomplished in bubble column reactors even at low temperatures and even in operations in atmospheric pressure. The reactors, which are unusual for this reaction, are otherwise known, to those skilled in the art, primarily for absorption processes, for example in exhaust gas purification.

Bubble column reactors are simple apparatuses without stirrers, in which temperature, pressure and in particular the liquid residence times can be adjusted in broad ranges, so that a variable procedure is available.

The invention therefore relates to a process for the preparation of an aromatic carbonate of the formula $$R^1\text{—O—CO—O—}R^2 \qquad (I)$$

in which
  $R^2$ denotes phenyl or naphthyl each of which may be monosubstituted to trisubstituted by straight-chain or branched $C_1$–$C_4$-alkyl, straight-chain or branched $C_1$–$C_4$-alkoxy, cyano and/or halogen, and
  $R^1$, independently of $R^2$, assumes the range of meanings of $R^2$ or denotes straight-chain or branched $C_1$–$C_6$-alkyl,
by catalysed reaction of 0.1 to 10 mol, preferably 0.2 to 5 mol, particularly preferably 0.5 to 3 mol, of an organic carbonate having at least one aliphatic ester group of the formula $$R^1\text{—O—CO—O—}R^3 \qquad (II)$$

in which
  $R^3$ denotes straight-chain or branched $C_1$–$C_6$-alkyl and
  $R^1$ has the above range of meanings,
with 1 mol of a phenolic compound of the formula $$R^2\text{—OX} \qquad (III)$$

in which
  $R^2$ has the above range of meanings and
  X represents hydrogen or —CO—O—$C_1$–$C_6$-alkyl having a straight-chain or branched alkyl group, in the presence of a transesterification catalyst known per se at 80° to 350° C., which is characterized in that the reaction is carried out in a bubble column reactor or a cascade of at least two bubble columns in such a way that the phenolic compound of the formula (III) is metered in in liquid form into the first bubble column and the organic carbonate of the formula (II) is metered in in the liquid or gaseous state simultaneously into each individual bubble column, but preferably only into the last bubble column, in the case of liquid metering, an evaporation of (II) in the bubble column proceeding, and the reaction products of the formula (I) are taken off from the last bubble column in liquid form and simultaneously at the upper end of each individual bubble column, preferably at the upper end of the first bubble column, the products of the formula $$R^3\text{—OX} \qquad (IV)$$

in which $R^3$ and X have the meaning mentioned, are taken off in gaseous form.

BRIEF DESCRIPTION OF THE DRAWINGS

Accompanying FIGS. 1 and 2 demonstrate by way of example variants of the inventive process using several bubble columns.

DETAILED DESCRIPTION OF THE INVENTION

Figure 1:
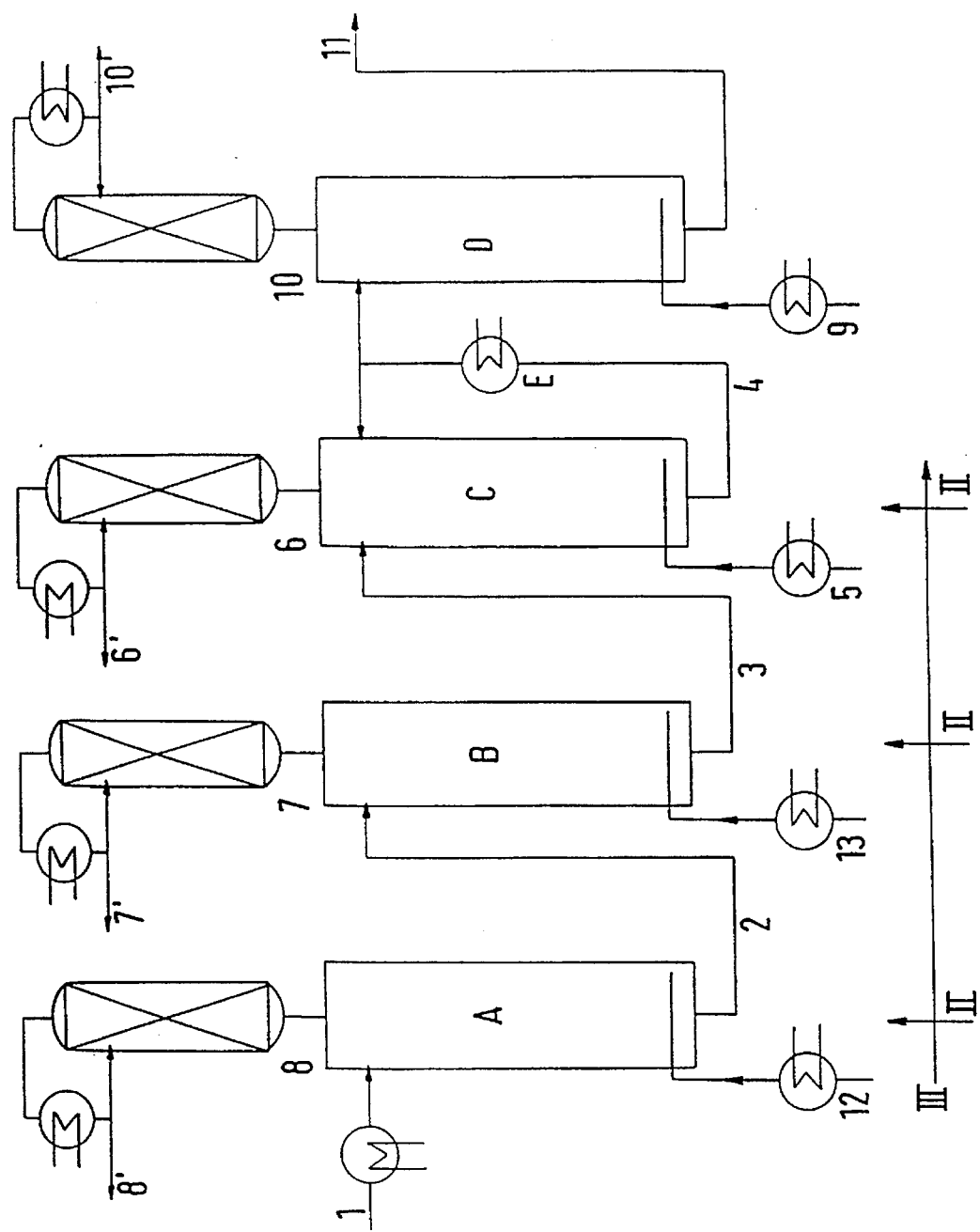

The transesterification by the process according to the invention includes a plurality of reactions, as the equations below show in generalized form (Alk=alkyl; Ar=aryl ):

$$\text{Alk—O—CO—O—Alk+Ar—OH} \rightarrow \text{Alk—O—CO—O—Ar+Alk—OH} \qquad \text{(Equation 1)}$$

$$\text{Alk—O—CO—O—Ar+Ar—OH} \rightarrow \text{Ar—O—CO—O—Ar+Alk—OH} \qquad \text{(Equation 2)}$$

$$2\text{Ar—OCO—O—Alk} \rightarrow \text{Ar—OCO—O—Ar+Alk—OCO—O—Alk} \qquad \text{(Equation 3)}$$

In the formation of a diaryl carbonate, the transesterification of the aliphatic ester groups to the aromatic ester groups proceeds in two stages, an alkyl aryl carbonate being proceeded through according to equation 1 as a product of the first transesterification stage.

Equation 3 further shows a disproportionation reaction in which both the symmetrical dialkyl carbonate and the desired symmetrical diaryl carbonate result from a mixed alkyl aryl carbonate. It is further possible to obtain the alkyl aryl carbonate as the desired reaction product, that is essentially only to operate the first transesterification stage. It is yet further possible to also obtain asymmetrical diaryl carbonates by use of mixtures of different phenols.

Dialkyl carbonates having identical or different aliphatic ester groups having straight-chain or branched $C_1$–$C_6$-alkyl are used. Such dialkyl carbonates are known to those skilled ill the art and can be prepared by known methods. For economic reasons, symmetrical dialkyl carbonates are generally used as starting material.

Straight-chain or branched $C_1$–$C_6$-alkyl is, for example, methyl, ethyl, propyl, isopropyl, butyl, isobutyl, pentyl or hexyl, preferably methyl or ethyl, particularly preferably methyl.

Straight-chain or branched $C_1$–$C_4$-alkoxy is, for example, methoxy, ethoxy, propoxy, isopropoxy, butoxy or isobutoxy, preferably methoxy.

Halogen is, for example, fluorine, chlorine or bromine, preferably fluorine or chlorine, particularly preferably chlorine.

The aromatic ester group can be derived from a phenol or a naphthol, preferably from a phenol and can be monosubstituted to trisubstituted in the manner stated, preferably monosubstituted or disubstituted, particularly preferably monosubstituted. The cyano substituent generally occurs only singly as a substituent. The process according to the invention has high particular importance for the transesterification of unsubstituted phenol.

Phenols which can be used according to the invention and which are included under the formula (III) when X represents hydrogen are, for example, unsubstituted phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol and 2-naphthol.

Phenolic compounds which can preferably be used are therefore generally those of the formula $$R^{12}\text{—OH} \qquad (V)$$

in which

R$^{12}$ denotes phenyl or phenyl monosubstituted by C$_1$–C$_4$-alkyl, C$_1$–C$_4$-alkoxy or chlorine.

Among these, unsubstituted phenol is particularly preferred.

The organic carbonates having at least one aliphatic ester group preferably used are symmetrical dialkyl carbonates of the formula $$R^3\text{—O—CO—O—}R^3 \qquad (VI)$$

in which

R$^3$ has the meaning given.

Dialkyl carbonates which can be used according to the invention are, for example, dimethyl carbonate, diethyl carbonate, dipropyl carbonate, dibutyl carbonate and dihexyl carbonate. Dialkyl carbonates which can preferably be used are dimethyl and diethyl carbonate, particularly preferably dimethyl carbonate (DMC).

The organic carbonate (II) having at least one aliphatic ester group can be used as such in the process according to the invention. However, it is possible, and represents a preferred variant, to use this organic carbonate in a mixture with small amounts of the underlying alcohol R$^3$—OH. The alcohol R$^3$—OH occurs as an elimination product in the process according to the invention and signifies the special case of the formula (IV) with X=H. The elimination products carbonate (X=—CO—O—C$_2$–C$_6$-alkyl) and alcohol (X=H) therefore do not need to be completely separated for return of the carbonate to the process according to the invention; this signifies an energetic advantage. The amount of the alcohol permissible in the mixture with the carbonate is 0–5% by weight, preferably 0.1–3% by weight, particularly preferably 0.15–2% by weight, based on the amount of carbonate used. The lower limit zero indicates the operation with pure carbonate.

Diaryl carbonates which can be prepared according to the invention are, for example, diphenyl carbonate, the symmetrically and asymmetrically substituted isomeric biscresyl carbonates, the symmetrically and asymmetrically substituted isomeric bis(chlorophenyl) carbonates, the symmetrically and asymmetrically substituted isomeric bis(methoxyphenyl) carbonates, the symmetrically and asymmetrically substituted isomeric bis(ethoxyphenyl) carbonates, bis(2,6-dimethylphenyl) carbonate, bis(2,4-dimethylphenyl) carbonate, di-1-naphthyl carbonate and di-2-naphthyl carbonate, furthermore other asymmetrically substituted diaryl carbonates, for example the isomeric cresyl phenyl carbonates, the isomeric chlorophenyl phenyl carbonates, the isomeric methoxyphenyl phenyl carbonates, the isomeric naphthyl phenyl carbonates and 1-naphthyl 2-naphthyl carbonate.

Diaryl carbonates which can preferably be prepared according to the invention are those of the formulae $$R^{15}\text{—OCOO—}R^{12} \qquad (VII)$$

and $$R^{12}\text{—OCOO—}R^{12} \qquad (VIII)$$

in which

R$^{12}$ and R$^{15}$, independently of each other, have the range of meanings given above for R$^{12}$.

A diaryl carbonate which can be particularly preferably prepared is diphenyl carbonate.

Alkyl aryl carbonates which can be prepared according to the invention are, for example, C$_1$–C$_6$-alkyl phenyl carbonates, such as methyl phenyl carbonate, ethyl phenyl carbonate, propyl phenyl carbonate, butyl phenyl carbonate and hexyl phenyl carbonate, C$_1$–C$_6$-alkyl (o-, m-, p-cresyl) carbonates, such as methyl o-cresyl carbonate, methyl p-cresyl carbonate, ethyl o-cresyl carbonate, ethyl p-cresyl carbonate, C$_1$–C$_6$-alkyl (o-, m-, p-chlorophenyl) carbonates, such as methyl p-chlorophenyl carbonate or ethyl p-chlorophenyl carbonate and analogous compounds. Alkyl aryl carbonates which can be particularly preferably prepared are methyl phenyl carbonate and ethyl phenyl carbonate, very particularly preferably methyl phenyl carbonate.

The bubble column reactors which can be used in the process according to the invention are the following types: simple bubble columns, cascades of simple bubble columns, bubble columns having internals and cascades of these bubble columns, such as: bubble columns having parallel chambers, cascade bubble columns, bubble columns having packings, bubble columns having static mixers, pulsed sieve-tray bubble columns, and other bubble column reactors known to those skilled in the art (H. Gerstenberg, Chem. Ing. Tech. 61 (1979) No. 3, p. 208–216; W. D. Deckwer, Reaktionstechnik in Blasensäulen [Reaction Technique in Bubble Columns], Otto Salle Verlag (1985)).

In the preferred embodiment, the bubble column reactors or cascades of bubble column reactors below are used: simple bubble columns, cascade bubble columns, bubble columns having parallel chambers and bubble columns having static mixers or packings.

In a further preferred embodiment, combinations both of the individual bubble column reactors in a cascade of bubble columns and in a cascade bubble column can also be used.

To maintain as homogeneous as possible a bubble flow through the liquid, distribution and redispersion elements can be mounted in the bubble column reactor along the longitudinal axis.

The fixed redispersion elements which are used are single-hole trays, perforated plates, sieve trays and other internals known to those skilled in the art which, when backmixing is effectively avoided, enable the counter-flow of gas phase and liquid phase.

In the individual cascade bubble column reactors, after the first dispersion of the gas phase, a further 0 to 20, preferably 1 to 15, redispersion elements can be present. In this case, a bubble column having 0 redispersion elements signifies the special case of a simple bubble column. The total number of the redispersion elements in a cascade of bubble columns can thus be 100, preferably 75, particularly preferably up to 60.

In the counter-current flow of the liquid phase and gas phase in cascade bubble columns, the liquid can either flow through the dispersion elements or flow through internal and/or external overflow pipes to the bubble column sections situated beneath.

For the initial dispersion of the gaseous carbonate of the formula (II) in the liquid phase at metering, conventional apparatuses can be used, such as porous sinter plates, perforated plates, sieve trays, push-in pipes, nozzles, ring spargers and other dispersion apparatuses known to those skilled in the art.

Within a bubble column, or, in the case of the use of a cascade of bubble columns, also within an individual bubble column, various types of the abovementioned dispersion elements can be present simultaneously, that is, for example, fixed internals as well as packings.

The liquid holdup in the bubble column reactors is more than 40%, preferably more than 50%, and particularly preferably more than 75%, of the available volume.

The gas velocity, based on the empty reactor cross-section, is 0.1 to 100 cm/s, preferably 1 to 50 cm/s and particularly preferably 2 to 30 cm/s.

The slenderness ratio of the bubble column reactors (ratio of length to diameter) is 1 to 30, preferably 1–20.

For the case that bubble column reactors having parallel chambers are used, the ratio of length to overall diameter of the bubble column can deviate from these figures, since here the individual chambers are to be taken into account.

For the supply of heat to the bubble columns, external heaters are suitable, such as jacket heaters, heat exchangers for liquids taken off intermediately or internal heat exchangers, such as parallel single tubes, transverse tube bundles, longitudinal tube bundles, spiral pipe coils, helical pipe coils, jacketed draught tubes and other heat exchange apparatuses known to those skilled in the art as prior art. In a preferred embodiment, the internal heat exchangers can additionally assume directional functions for the liquid flow and the gas dispersion.

To separate off the more readily volatile components from the liquid phase produced at the lower end, a stripping column can be installed according to the prior art. In the same way, to purify the gas phase, produced from dialkyl carbonate and the relevant alcohol, from the aromatic hydroxyl compound and the transesterification products alkyl aryl carbonate and diaryl carbonate, the upper end of the bubble column can be equipped with an enrichment column.

In a further procedure, additionally to the starting materials, a solvent inert under the reaction conditions which evaporates in the bubble column or gas can be fed into the apparatus at any desired position. Such inert solvents are, for example, hydrocarbons, such as hexane, heptane, i-octane, methyl-cyclopentane, cyclohexane, methylcyclohexane, toluene, xylenes, chlorobenzenes, Tetralin, Dekalin etc. Inert gases which are useful are, for example, carbon dioxide, nitrogen, noble gases etc. These inert solvents and gases can also be metered in together with the gaseous carbonate or the carbonate to evaporate in the bubble column and can be varied in a broad concentration range.

In some embodiments it can be expedient also to meter the pure inert gas or solvent into one or more bubble columns.

For the case when DMC is used as aliphatic carbonate, it can be advantageous to use an inert solvent which forms an azeotrope with methanol and preferentially removes this from the bubble column. The removal of methanol from the equilibrium promotes the continuation of the process according to the invention.

Figure 2:
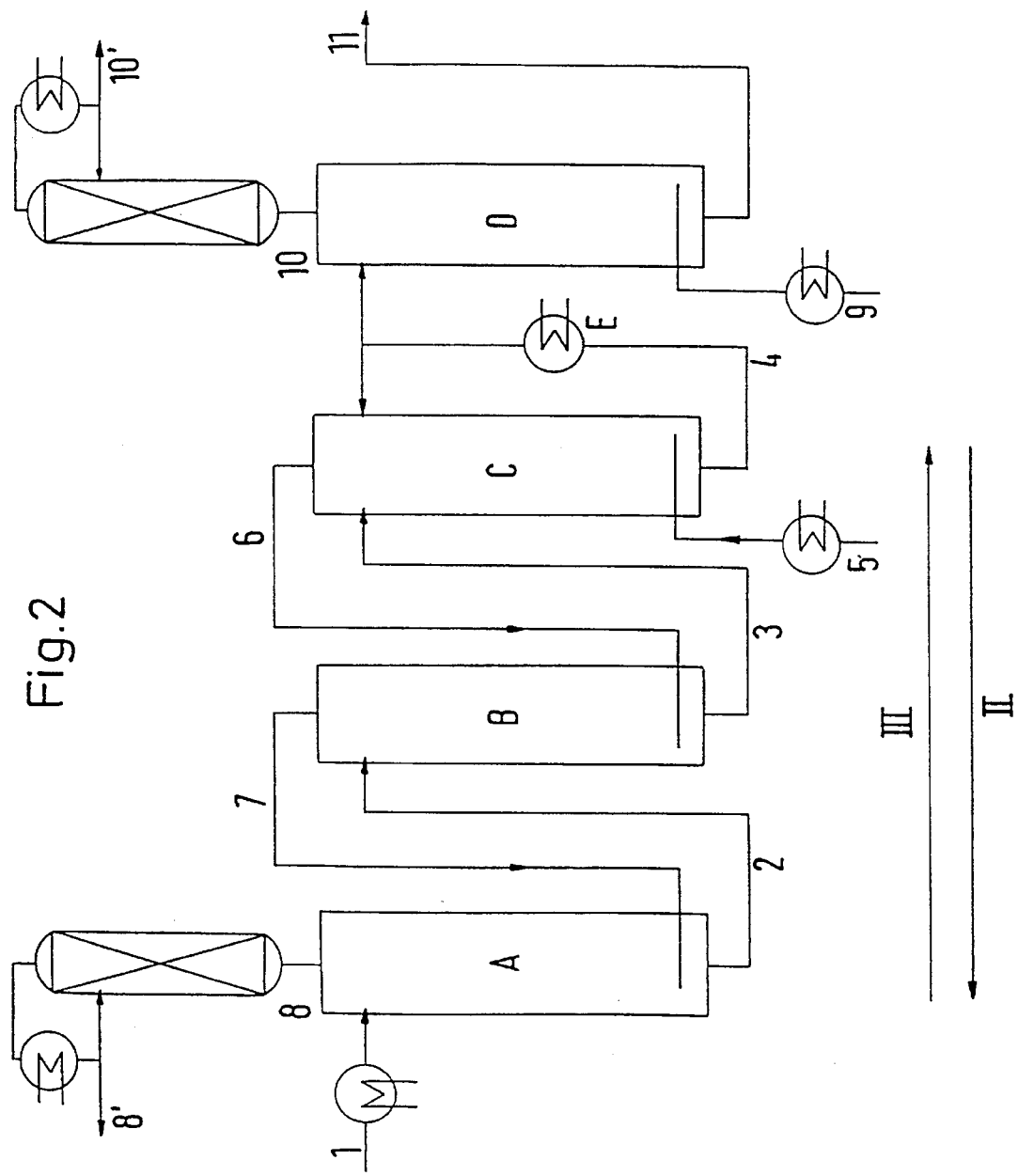

In FIGS. 1 and 2, different exemplary embodiments of the invention are shown. Numbers and letters quoted in the text refer to these figures.

Therein, the process according to the invention is preferably carried out using 1 to 18, particularly preferably 2 to 12 bubble column reactors, the lower limit 1 signifying carrying out the process in a single bubble column.

In the preferred embodiment, a cascade of cascade bubble column reactors is used (cascade bubble columns). In FIGS. 1 and 2, exemplary operations with 3 bubble column reactors (A, B and C) are depicted, in which the operation according to the invention is not intended to be restricted to these examples. D and E signify residence time vessels described later for the completion of the reaction and stripping sections of columns for mass separations, respectively.

The reaction component of the formula (III) metered into the first bubble column (A) can optionally be preheated in an upstream heater element to the intended reaction temperature. It is preferably introduced into the bubble column at the upper end in liquid form via line (1).

The liquid phase to be taken off from the particular bubble column is taken off at the lower end and metered in again at the upper end to the respective following bubble column B or C via the lines (2), (3) or (4). The regulation of the desired filling level in the continuously operated bubble column reactors is carried out according to the prior art.

When a bubble column cascade is used, the gas phase (II) can be fed through the continuously running liquid stream (III)+(I) either in cross-flow (FIG. 1) or preferably in counter-current (FIG. 2).

Cross-flow denotes in this case that the starting materials of the formula (II) are each metered into every bubble column reactor via the lines (12), (13), (5) (FIG. 1) and are each taken off again at the upper end of each bubble column via the lines (8), (7) and (6) (FIG. 1), that is the starting materials of the formula (II) flow through the bubble column reactors transversely to the direction of flow of the liquid phase (III)+(I). The total amount of the starting materials of the formula (II) metered in can in this case be apportioned as desired to the individual bubble column reactors. In the particular bubble column reactor, in this case, the counter-current mode of operation of liquid phase and gas phase is preferably realized.

The counter-current mode of operation preferably to be used (FIG. 2) denotes that the starting materials of the formula (II) are metered into the last bubble column reactor (in FIG. 2, reactor C), continuously conducted in the opposite direction to the liquid phase running from the first bubble column reactor to the last reactor (C in FIG. 2) and excess starting material (II) and product formed (IV) are taken off at the upper end of the first bubble column reactor (A in FIG. 2). If (II) and (IV) form an azeotrope, as in the case DMC/methanol, it can be expedient to take off some of such an azeotrope at the upper end of intermediate reactors as well.

The starting materials of the formula (II) and the inert compound optionally added can in both cases be either metered in in the liquid state and evaporated by the liquid phase present or, preferably, evaporated in an upstream apparatus and introduced in the gaseous state into the respective bubble column.

It is furthermore also possible to have the starting materials of the formula (II) flow partly in cross-flow and partly in counter-current to the liquid phase (III)+(I).

The reaction products of the formula (IV) to be taken off at the upper end of the respective bubble column can be taken off, for example, directly in the gaseous state via (6'), (7') and (8').

It is in this case possibly advantageous, by suitable dephlegmation or/and by an attached column to separate off previously higher-boiling reaction constituents, for example products of the formula (I) or starting materials of the formula (III), and to return them to the respective bubble column. The products of the formula (IV) can, for example, for this purpose be introduced without condensation to a suitable separation apparatus. In the case of the reaction of dimethyl carbonate with phenol, this could be a pressure distillation column for separating the dimethyl carbonate/methanol mixture produced, in order to keep as little as possible DMC in the top product of the separation column. The dimethyl carbonate produced in this case, which possibly still contains small amounts of methanol, can be returned as starting material of the formula (II) to the transesterification process.

In the same way, it is possible to take off the products of the formula (IV), if required after separating off higher-boiling reaction constituents, as described above, and to condense them. A purification and fractionation of the product stream can then be carried out in a suitable manner known to those skilled in the art.

The product stream to be taken off in the liquid state at the last reactor, for example C in FIGS. 1 and 2, can be separated off if required in a downstream stripping section (E in FIGS. 1 and 2) from low-boiling constituents, for example starting materials of the formula (II) or the products of the formula (IV), which are then returned to the reactors, for example the last bubble column of the cascade (C). The product stream taken off in the liquid state can be worked up and purified by conventional methods, for example by distillation.

In a particularly preferred embodiment, the product stream to be taken off in the liquid state is passed into 1 to 5, preferably 1 to 3 downstream reactors, a further reaction in the sense of equation 2 and/or 3 being able to proceed there. These reactors are, for example, additional bubble columns, stirred tanks or a reaction distillation which are treated with one or more inert compounds, gaseous under the reaction conditions (line (9), possibly via a preheater/evaporator). In FIGS. 1 and 2, this mode of operation is illustrated, simplified for clarity by a single bubble column reactor (D), in which the mode of operation according to the invention is not intended to be restricted hereby.

In this case, the aromatic carbonate of the formula (I) is taken off at (11) and the volatile reaction product produced in reactor D is taken off together with the gaseous compounds at (10').

The respective last residence time vessel D can optionally have a downstream stripping section by means of which low-boiling products of the formulae (IV)+(II) and/or unreacted starting materials of the formula (III) are completely or partly returned to this residence time vessel D. In the same way, it is possibly advantageous to separate off the volatile reaction products of the formula (IV), to be taken off at the upper end of the first residence time vessel D for example via (10'), from higher-boiling products of the formula (I) or starting materials of the formula (III) via an enrichment and/or dephlegmator section attached there via the line (10) and to return these to D.

The gaseous compounds in the meaning just mentioned of the invention which are used are for example superheated phenol, inert gases alone, such as nitrogen, noble gases, carbon dioxide, $C_1$–$C_{12}$-alkanes, cyclic alkanes, such as cyclohexane, Dekalin, aromatic hydrocarbons, such as benzene, toluene, xylenes, cumene, mesitylene, and mixtures of inert gases or mixtures of phenol with inert gas. In the preferred embodiment, easily condensable compounds, such as phenol, toluene, mesitylene, Dekalin, alone or as mixtures, are used. However, for the case that only the first transesterification stage according to equation (1) is desired, it is entirely possible to introduce dialkyl carbonate, optionally in a mixture with inert gas, into all or individual bubble columns and into the residence time vessels. Such an inert gas can advantageously in turn be an azeotrope-former for alkanol to be discharged.

The product stream taken off in the liquid state at the bubble column reactor or, possibly, at the last reactor of a bubble column cascade after the 1st transesterification stage, which contains the products of the formula (I) particularly according to equation (1), to a lesser extent also according to equations (2) and (3) can, in a further particular embodiment of the invention, with or without intermediate storage in suitable vessels, be metered in place of the starting material of the formula (III) back into the bubble column reactor or, possibly, into the 1st bubble column of a bubble column cascade, in order to carry out or complete the 2nd transesterification stage according to equation (2) or a disproportionation according to equation (3). This is also optionally possible repeatedly, the feed of the second starting material of the formula (II) also, optionally, being able to be omitted and replaced by inert compounds gaseous under reaction conditions. To continuously carry out such a mode of operation, for example, either at least two storage vessels or one storage vessel having at least two chambers are necessary, the product from the running reaction being fed into the 1st chamber and the starting material for the running reaction being taken off from the 2nd chamber. When one chamber is emptied or one chamber is filled, the 2nd chamber is used for receiving the product from the bubble column reactor or from the last reactor of a bubble column cascade and the 1st chamber is used for feeding the starting material into the bubble column reactor or into the bubble column cascade.

Alternatively, in a further embodiment, a further treatment of the liquid reaction product from the 1st transesterification stage can be carried out, as for example in FIGS. 1 and 2 the outflow of line (4) to reactor (C), in a multiple-stage distillation apparatus in the meaning of EP 0 461 274, a further reaction being able to proceed there according to equation (2) and/or (3).

In a further variant, the residence time vessel D is designed in the form of a distillation apparatus which is operated in the meaning of a "reaction distillation", that is, simultaneously to the proceeding reaction, a distillation of the participating substances is carried out.

The essential characteristics of a "reaction distillation" in the meaning of the invention are the following: the as yet unreacted alkyl aryl carbonate intermediate from the 1st transesterification stage is substantially prevented, by a specially selected temperature gradient in the distillation apparatus, from leaving the reaction section of the reactor at the top or at the bottom. The readily volatile reaction products of the formula (IV) are taken off at the head of the column, the poorly volatile reaction product, here the diaryl carbonate (2nd transesterification stage), is taken off at the foot of the column. Any excess phenol possibly present can be taken off together with the diaryl carbonate end products at the foot of the distillation apparatus or together with the low-boiling products at the head of the apparatus.

The reactor designated as a "reaction column" is composed of a column-like tube to which is applied a temperature profile which includes a temperature range increasing from top to bottom of 60° to 320° C., preferably 65° to 305° C. and particularly preferably 65° to 250° C. To establish the temperature gradients in the individual sections of the column-like reactor, these sections can be provided with insulation or thermostatting. The thermostatting in this case can signify heating or cooling as required. The reaction column can be expanded or contracted in various sections of its overall length, in correspondence with the gas and liquid loadings and the required residence times.

Fixed internals are preferred for the central part of the reaction column, the reaction region, and in contrast, loose packings and fixed packings are preferred for the parts in which separations take place.

At the lower end of the reaction column are arranged one or more evaporators, optionally separated by adiabatically insulated column parts. These evaporators can be arranged inside or outside the column. In an industrial embodiment, equipment conventional in the technology, such as circulation evaporators, falling film evaporators and spiral tube evaporators is used.

Above the evaporator zone, in the central region designated as "reaction zone", fixed internals or, for example, bubble-cap trays are preferably used. The theoretical number of plates in this region is 1 to 50, preferably 1 to 25 and particularly 1 to 15.

Above this region in turn, the column is equipped with further loose packings, packings or internals particularly suitable for mass separations by distillation. At the upper end of the column an enrichment section is preferably arranged, by means of which a specific reflux to the column can be established.

The reaction column is operated in such a way that the product stream from the 1st transesterification stage, taken off in the liquid state from the bubble column reactor or the bubble column cascade, is metered in in the liquid state above the "reaction zone". This stream passes through the "reaction zone" and is there partly converted into diaryl carbonate according to equations (2) and (3) and the as yet unreacted reactants are transported in the gaseous state with the aid of the described evaporators back to the reaction zone and the upper parts of the column. These condense there and react afresh to give the diaryl carbonate end product. The diaryl carbonate end product is enriched in the bottom region of the column as the highest boiling reaction component and is there fed out together with any homogeneously dissolved catalyst and small amounts of alkyl aryl carbonate and aromatic hydroxyl compound.

The readily volatile reaction products of the formula (IV) are taken off at the head of the column. The phenols of the formula (III), present in excess or unreacted, can be fed out at the foot of the column with the diaryl carbonate end product of the formula (I) or, in a preferred mode of operation, with the low-boiling products at the head of the column.

In a further procedure, the product stream to be taken off in the liquid state can be passed into 1 to 5, preferably 1 to 3, downstream residence time vessels D, optionally stirred or treated with inert gas, further reactions according to equation 2 and/or equation 3 being able to proceed there. In this case, the aromatic carbonate of the formula (I) is taken off at (11) and volatile reaction products produced in D are taken off at (10) or (10').

To mix the reaction components, the stirred vessels to be used according to the invention are equipped with agitators usable therefor. Such stirrers are known to those skilled in the art. The following can be mentioned by way of example: disc stirrers, impeller stirrers, propeller stirrers, paddle stirrers, MIG stirrers and Intermig stirrers, tubular stirrers and other hollow stirrer types. Preferred stirrers are those which permit an effective mixing of gases and liquids, for example hollow stirrers, such as tubular stirrers and triangular stirrers, propeller stirrers, turbine stirrers etc.

For improved mixing, the stirred vessels can preferably be provided with flow-breaker internals. These flow breakers can simultaneously be designed to be thermostattable for introducing heat into the reactor or conducting heat away from the reactor.

Those modes of operation and embodiments of the invention are preferably used in which additional residence time vessels are used in the form of columns or stirred tanks.

Possible embodiments in terms of apparatus for carrying out the process according to the invention are the following, the listing being in no way exhaustive:

a bubble column, a bubble column having a residence time vessel in the form of a stirred tank and/or a distillation column, a bubble column having a plurality of residence time vessels in the form of stirred tanks and/or distillation columns, a cascade of two or more bubble columns, a bubble column cascade of two or more bubble columns having a residence time vessel in the form of a stirred tank or a distillation column, a cascade of two or more bubble columns having a plurality of residence time vessels in the form of stirred tanks and/or distillation columns, in all cases bubble columns being able to be used without or with internals of the type mentioned.

The heat of reaction necessary for the reaction can be introduced with the starting materials. However, it is preferred to introduce additional energy into the reactor for example via a jacket heating and/or by internal heating elements.

The further work-up of the reaction products of the formula (I), taken off in the liquid state via line (11), which can contain excess phenolic compound (III) and, possibly, further, a homogeneous dissolved catalyst, can be carried out by conventional methods, for example by distillation.

In a preferred embodiment, if a titanium compound, for example titanium tetraphenolate, is used as catalyst, this can be separated off from the reaction product of the 2nd transesterification stage before the work-up by distillation of the liquid reaction product by crystallization and subsequent filtration or sedimentation.

For the separation, the liquid reaction mixture is cooled for this purpose to a temperature of 40° to 120° C., preferably 50° to 100° C., particularly preferably 60° to 90° C., this mixture having to remain liquid. The sedimented titanium-containing precipitate can then be separated off. The remaining reaction mixture contains residual titanium amounts of less than 100 ppm. The catalyst thus separated off can be returned, if required without further purification, to the process.

By the cooling according to the invention of the reaction mixture and separating off of the sedimented, titanium-containing precipitate, in a surprisingly simple operation, a reaction mixture is obtained which can be worked up both by crystallization and by distillation under conditions conventional per se for isolating the aromatic carbonate, without the fear of loss of yields. Special reaction conditions and special precautionary measures which would be required by the presence of the catalyst are therefore no longer required.

The separation of the titanium catalyst can optionally also be carried out even after the first transesterification stage (after reactor (C) in FIGS. 1 and 2), if, for example, an alkyl aryl carbonate is desired or another catalyst is intended for the 2nd transesterification stage.

The transesterification catalysts to be used and known as such are preferably introduced in dissolved or suspended form into the bubble column reactor or the bubble column cascade together with the starting materials of the formula (III) to be metered in in the liquid state. Alternatively, the catalyst can also be metered in separately or dissolved or suspended in a small amount of the starting material of the formula (III) or in a suitable inert solvent, see above, external to the system. In the case of the use of heterogeneous catalysts, these can also be used directly in an immobile state in the bubble column reactor or in the bubble column cascade.

A suitable filter apparatus must prevent the discharge of the catalysts in this case.

It is important that a catalyst is present on at least 2 distribution elements in a cascade bubble column or in at least 2 bubble columns in a bubble column cascade.

In the case of the use of non-immobile catalysts, it is possible to return, as described above, the catalyst back to the reaction process, after partial or complete separation from the products or starting materials, if required a portion of the catalyst corresponding to the amount of catalyst deactivated being separated off and replaced by fresh catalyst.

The process according to the invention is carried out at temperatures in the liquid phase from 80° to 350° C., preferably at 100° to 250° C. and particularly preferably at temperatures from 120° to 240° C. The liquid phase temperature in the bubble column reactors should not exceed the evaporation temperature of the phenolic compound of the formula (III) used or of the phenolic solution used. It can therefore be advantageous to carry out the transesterification according to the invention in the region of the bubble column reactors not only at atmospheric pressure but also at elevated or reduced pressure in the range from 10 mbar to 20 bar. A preferred pressure range is between 0.05 and 15 bar, and a particularly preferred pressure range is between 0.08 and 13 bar. In this case it can be expedient to operate the individual reactors of a cascade each at individual pressures. With the pressures the temperature can be varied if required in the individual bubble column reactors of a cascade. In a preferred embodiment, for example, both pressure and temperature can decrease from the 1st to the last bubble column reactor.

Catalysts which are useful for the process according to the invention and which can be identical for all phases of the process according to the invention are known in the literature. Such catalysts are, for example, hydrides, oxides, hydroxides, alcoholates, amides or salts of alkali(alkaline earth) metals, such as lithium, sodium, potassium, rubidium, caesium, magnesium and calcium, preferably of lithium, sodium, potassium, magnesium and calcium, particularly preferably of lithium, sodium and potassium (U.S. Pat. No. 3,642,858, U.S. Pat. No. 3,803,201, EP 1082). For the case of the use of the alcoholates, these can also be formed according to the invention in situ by use of the elemental alkali metals and the alcohol to be reacted according to the invention. Salts of the alkali(alkaline earth) metals can be those of organic or inorganic acids, such as of acetic acid, propionic acid, butyric acid, benzoic acid, stearic acid, carbonic acid (carbonates or hydrogen carbonates), of hydrochloric acid, hydrobromic or hydriodic acid, nitric acid, sulphuric acid, hydrofluoric acid, phosphoric acid, hydrocyanic acid, thiocyanic acid, boric acid, stannic acid, $C_1$–$C_4$-stannonic acids or antimonic acids. Preferably, compounds of the alkali(alkaline earth) metals which are useful are the oxides, hydroxides, alcoholates, acetates, propionates, benzoates, carbonates and hydrogen carbonates, particularly preferably used being hydroxides, alcoholates, acetates, benzoates or carbonates.

Such alkali(alkaline earth) metal compounds (optionally formed in situ from the free alkali metals) are used in amounts of 0.001 to 2% by weight, preferably 0.005 to 0.9% by weight, particularly preferably 0.01 to 0.5% by weight, based on the reaction mixture to be reacted.

Further catalysts which can be used according to the invention are Lewis acid metal compounds such as $AlX_3$, $TiX_3$, $UX_4$, $TiX_4$, $VOX_3$, $VX_5$, $ZnX_2$, $FeX_3$ and $SnX_4$, in which X represents halogen, acetoxy or aryloxy (German Offenlegungsschrift 2 528 412, 2 552 907), for example titanium tetrachloride, titanium tetraphenoxide, titanium tetraethoxide, titanium tetraisopropylate, titanium tetradodecylate, tin tetraisooctylate and aluminium triisopropylate, furthermore organotin compounds of the general formula $(R^4)_{4-x}$—$Sn(Y)_x$, in which Y represents a radical $OCOR^5$, OH or OR, where $R^5$ denotes $C_1$–$C_{12}$-alkyl, $C_6$–$C_{12}$-aryl or $C_7$–$C_{13}$-alkylaryl and $R^4$, independently of $R^5$, can assume the range of meanings of $R^5$ and x denotes an integer from 1 to 3, dialkyltin compounds having 1 to 12 C atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyl dimethoxytin, dimethyltin glycolate, dibutyl diethoxytin, triethyltin hydroxide, hexaethylstannoxane, hexabutylstannoxane, dibutyltin oxide, dioctyltin oxide, butyltin triisooctylate, octyltin triisooctylate, butylstannonic acid and octylstannonic acid in amounts of 0.001 to 20% by weight (EP 879, EP 880, EP 39 452, German Offenlegungsschrift 3 445 555, JP 79/62 023), polymeric tin compounds of the formula —[—$R^4,R^5Sn$—O—]—, for example poly[oxy (dibutyl stannylene)], poly[oxy (dioctylstannylene)], poly[oxy(butylphenylstannylene)] and poly[oxy (diphenyl-stannylene)] (German Offenlegungsschrift 3 445 552), polymeric hydroxystannoxanes of the formula —[$R^4Sn(OH)$—O—]—, for example poly(ethylhydroxystannoxane), poly(butyl-hydroxystannoxane), poly(octylhydroxystannoxane), poly(undecylhydroxystannoxane) and poly(dodecylhydroxystannoxane) in amounts of 0.001 to 20% by weight, preferably from 0.005 to 5% by weight, based on dicarbonate (DE 4 006 520). Other tin compounds which can be used according to the invention are Sn(II) oxide or have the formula $$X^1-Sn(R^4)_2-O-Sn(R^4)_2-X^2 \qquad (IX)$$

in which $X^1$ and $X^2$, independently of each other, denote OH, SCN, $OR^4$, $OCOR^4$ or halogen and $R^4$ denotes alkyl, aryl (EP 338 760).

Other catalysts which can be used according to the invention are lead compounds, optionally together with triorganophosphanes, with a chelate compound or with an alkali metal halide, for example $Pb(OH)_2$—$2PbCO$, $Pb(OCO$—$CH_3)_2$, $Pb(OCO$—$CH_3)_2$—$2LiCl$, $Pb(OCO$—$CH_3)_2 2PPh_3$ in amounts of 0.001 to 1, preferably from 0.005 to 0.25 mol per mol of carbonate (JP 57/176 932, JP 01/093 580), other lead (II) and lead (IV) compounds, such as PbO, $PbO_2$, red lead oxide plumbites ($PbO_2^{2-}$) and plumbates ($PbO_3^{2-}$) (JP 01/093 560), iron(III) acetate (JP 61/172 852), furthermore copper salts and/or metal complexes, for example of alkali metal, zinc, titanium and iron (JP 89/005 588), combinations of Lewis acids and proton acids (German Offenlegungsschrift 3 445 553) or element compounds of Sc, Cr, Mo, W, Mn, Au, Ga, In, Bi, Te and lanthanides (EP 338 760).

Furthermore, heterogeneous catalyst systems are usable in the process according to the invention. These are for example mixed oxides of silicon and titanium which can be prepared by collective hydrolysis of silicon halides and titanium halides (JP 54/125 617) and titanium dioxides with a high BET surface area >208 $m^2$/g (German Offenlegungsschrift 4 036 594).

Catalysts which can preferably be used in the process according to the invention are tin compounds, titanium compounds and zirconium compounds and the abovementioned alkali metal compounds and alkaline earth metal compounds, catalysts which are particularly preferably usable are organotin compounds and titanium tetra-alcoholates and tetraphenolates.

The amounts of catalyst to be used are 0.01 to 10 mol %, preferably 0.05 to 5 mol % and particularly preferably 0.01 to 2 mol %, based on the phenol component or alkyl aryl carbonate component used and can sometimes differ from the amounts mentioned in the literature.

The following examples are intended to describe the present invention concretely, it not being intended to be restricted to these examples.

EXAMPLES

Example 1

Figure 3:
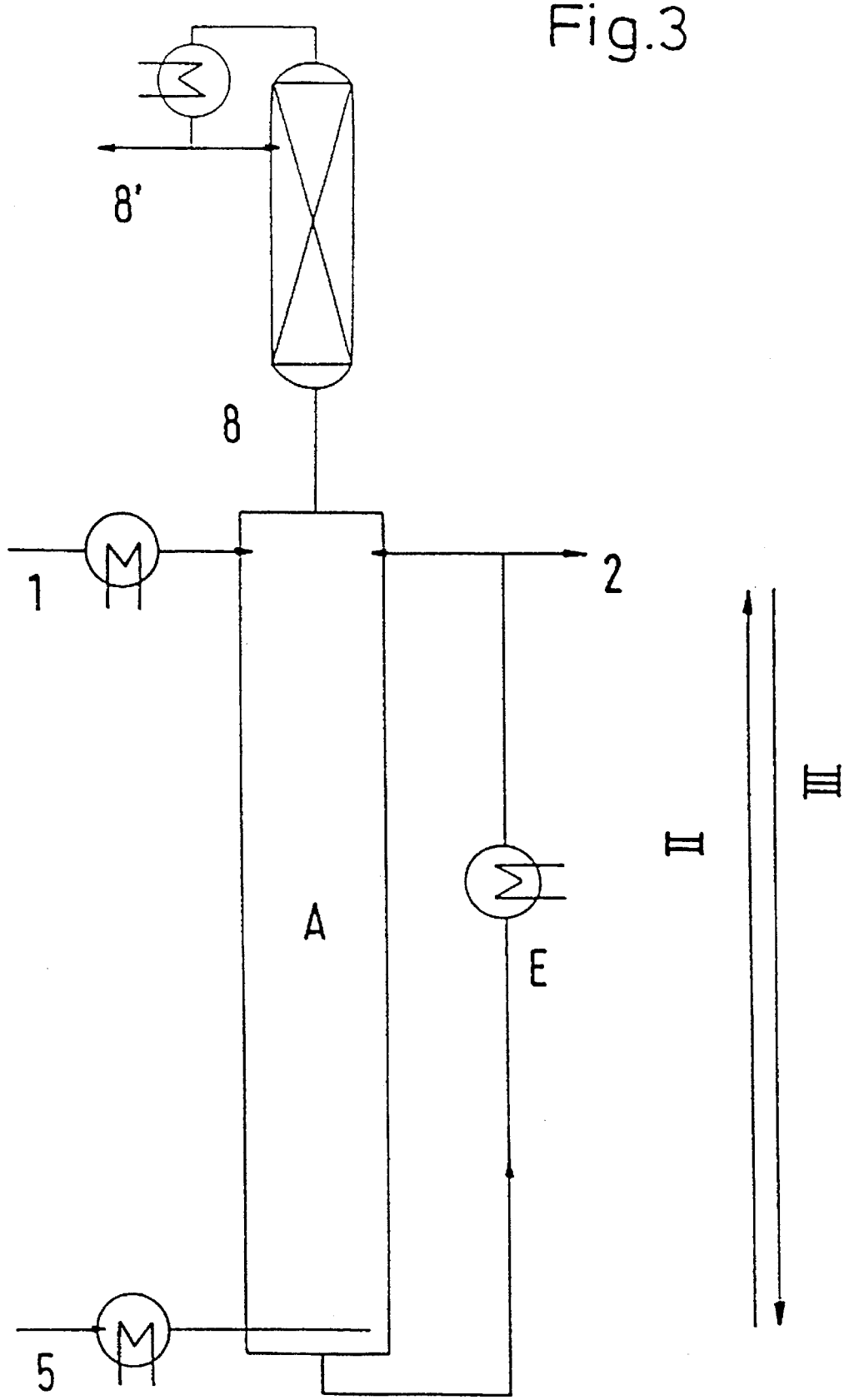
FIG. 3 demonstrates a variant with only one bubble column which was used for the working examples.

(For equipment see FIG. 3; it depicts an embodiment having only one bubble column. The reference numbers have the meaning given above, in which metering is performed via line (2) not as in FIGS. 1 and 2 into the next bubble column, but as the reaction mixture is taken off).

For this example, a bubble column was used (l=60 cm, d=4.5 cm having 10 perforated plates for dispersing the gas phase) having an internal volume of 950 ml, provided with a heating jacket and heatable by an oil thermostat. The metering of the liquid phase was performed at the upper end of the bubble column via a heated line and the takeoff was performed at the bottom end via a heated height-adjustable siphon. The gas phase was fed in at the lower end of the bubble column via a glass sinter plate and taken off at the head via a column 30 cm long filled with Raschig rings and having an attached column head which permitted the establishment of a reflux to the bubble column reactor.

The bubble column was filled with 850 ml of phenol and the reactor jacket was thermostatted with oil to 180° C. Via a heated pump, 500 g/h of a mixture of 97.8% by weight of phenol and 2.2% by weight of titanium tetraphenolate (liquid phase) were metered in continuously at the upper end of the bubble column reactor and, at the same time, 500 g/h of dimethyl carbonate (DMC), which was continuously evaporated in an electrically heated tube, was metered in at the lower end. After 4 h, the reaction was in equilibrium, that is the composition of the gas phase and the liquid phase no longer changed. At the reactor outlet, 557 g/h of product mixture containing 65.7 g/h of methyl phenyl carbonate (MPC) and 13.5 g/h of diphenyl carbonate (DPC) were taken off via the siphon. The rest making up 100% was phenol, little dimethyl carbonate and catalyst. At the upper end of the bubble column, a product mixture of methanol and DMC was taken off via the attached column. From this there results a space-time yield for the formation of MPC and DPC of 83.0 g/l h. The selectivity with respect to the formation of aromatic carbonates was >99.9%.

Example 2

In the equipment described in Example 1 and under the reaction conditions specified there, 750 g/h of a mixture of 98.6% by weight of phenol and 1.4% by weight of octylstannonic acid were fed in continuously at the upper end of the bubble column and 750 g/h of DMC at the lower end of the bubble column. After approximately 3 h, the reaction was in equilibrium. 793 g/h of liquid product mixture containing 105.6 g of MPC and 23 g/h of DPC were continuously taken off and at the upper end of the bubble column a mixture of methanol and DMC was taken off. This corresponds to a space-time yield for MPC and DPC of 135 g/l h. The selectivity was >99.9%.

Example 3

For this example, a bubble column of 150 cm in length and 2.8 cm in diameter (923 ml internal volume) and having a packing of 3×3 mm V4A stainless steel wire mesh spirals was used. The reactor jacket was heated to 180° C. and the bubble column was filled with 600 ml of phenol. Analogously to Examples 1 and 2, 250 g/h of phenol were metered in together with 1.4% by weight of octylstannonic acid and 250 g/h of DMC. After approximately 3 h, the reaction was in equilibrium and 270 g/h of liquid product containing 51 g of MPC and 10.5 g of DPC were taken off via the siphon. This corresponds to a space-time yield of 66.6 g/l h. The selectivity here was also 99.9%.

Example 4

Example 2 was repeated with the reaction conditions and starting material streams specified there. In addition, continuous introduction of the liquid phase taken off at reactor A (FIG. 3) was carried out at the upper end of an additional bubble column reactor (reactor D in FIGS. 1 and 2). This bubble column reactor (of identical type to reactor A) was likewise provided with jacket heating (thermostatted with oil to 180° C.).

Simultaneously with the liquid phase, a nitrogen stream of 100 l (S.T.P.)/h was preheated in an electrically heated tube and metered in at the lower end of the additional bubble column. After 6 h, the reaction was in equilibrium.

At the lower end of the second bubble column, 767.3 g/h of liquid product mixture containing 21.1 g of MPC, 85.4 g of DPC and 660.8 g of phenol continuously ran off via an outlet. In a freezer trap, 25 g of a mixture of DMC and methanol condensed out of the nitrogen stream per hour. This corresponds to a space-time yield for MPC and DPC of 56.1 g/l h, based on the total reaction volume of the two reactors.

Comparative Example

A heated stirred vessel having 1 l internal volume, which was equipped with a 1 m long column filled with 4×4 mm glass rings was filled with 500 g of phenol and 11 g of titanium tetraphenolate. After heating up the vessel contents to 175° C. to 180° C., the metering in of the DMC was performed in such a way that the internal temperature did not decrease. In the course of 4 h, 78 g of DMC were metered in. At the same time, 49.1 g of a mixture of DMC and methanol distilled off via the column. The bottom product after this time was composed of 451.4 g of phenol, 58.5 g of MPC, 13 g of DPC, 2.2 g of by-products and 3.7 g of DMC. From this there results a phenol conversion rate of 9.7% and a selectivity of 97.9%, based on converted phenol. The space-time yield for the formation of the aromatic carbonates was thus 8.94 g/l h.

What is claimed is:

1. A process for the preparation of an aromatic carbonate of the formula $$R^1\text{—O—CO—O—}R^2 \qquad (I)$$

in which $R^2$ denotes phenyl or naphthyl each of which may be monosubstituted to trisubstituted by straight-chain or branched $C_1$–$C_4$-alkyl, straight-chain or branched $C_1$–$C_4$-alkoxy, cyano and/or halogen, and $R^1$ independently of $R^2$, assumes the range of meanings of $R^2$ or denotes straight-chain or branched $C_1$–$C_6$-alkyl, by catalyzed reaction of in each case 0.1–10 mol of an organic carbonate having at least one aliphaltic ester group of the formula $$R^1\text{—OCOO—}R^3 \qquad (II)$$

in which $R^3$ denotes straight-chain or branched $C_1$–$C_6$-alkyl and $R^1$ has the above range of meanings, with in each case 1 mol of a phenolic compound of the formula $$R^2\text{—OX} \qquad (III)$$

in which $R^2$ has the above range of meanings and

X represents hydrogen or —CO—O—$C_1$–$C_6$-alkyl having a straight-chain or branched alkyl group, in the presence of a transesterification catalyst at 80°–350° C. and 10 mbar to 20 bar, wherein the reaction is carried out in a bubble column reactor or a cascade of at least two bubble columns in such a way that the phenolic compound of the formula (III) is metered in liquid form into the first bubble column and the organic carbonate of the formula (II) is metered in the liquid or gaseous state simultaneously into each individual bubble column, in the case of liquid metering, an evaporation of (II) in the bubble column proceeding, and the reaction products of the formula (I) are taken off from the last bubble column in liquid form and simultaneously at the upper end of each individual bubble column the products of the formula $$R^3\text{—OX} \qquad (IV)$$

in which $R^3$ and X have the meaning mentioned, are taken off in gaseous form.

2. The process of claim 1, wherein a dialkyl carbonate of the formula $$R^3\text{—O—CO—O—}R^3 \qquad (VI)$$

in which $R^3$ denotes straight-chain or branched $C_1$–$C_6$-alkyl is reacted as the organic carbonate.

3. The process of claim 1, wherein a phenolic compound of the formula $$R^{12}\text{—OH} \qquad (V)$$

in which $R^{12}$ denotes phenyl or phenyl monosubstituted by $C_1$–$C_4$-alkyl, $C_1$–$C_4$-alkoxy or chlorine is reacted as the phenolic compound.

4. The process of claim 1, wherein 0.2–5 mol of organic carbonate is reacted with 1 mol of phenolic compound.

5. The process of claim 4, wherein 0.5–3 mol of organic carbonate is reacted with 1 mol of phenolic compound.

6. The process of claim 1, wherein, in the case of a cascade, the organic carbonate is metered in only into the last bubble column.

7. The process of claim 1, wherein the products of the formula (IV) are taken off in gaseous form, in the case of a cascade, at the upper end of the first bubble column.

8. The process of claim 1, wherein the reaction is carried out in 1 to 18 bubble columns.

9. The process of claim 8, wherein the reaction is carried out in 2 to 12 bubble columns.

10. The process of claim 1, wherein the reaction is carried out in at least two sequentially-connected bubble column reactors in such a way that the organic carbonate of the formula (II) is metered into the first bubble column and the aromatic carbonate of the formula (I) is taken off in liquid form from the last bubble column and the product of the formula (IV) is taken off at the upper end of the first bubble column.

11. The process of claim 1, wherein a temperature of 100°–250° C. is employed, in the case of a bubble column cascade, the temperatures in the bubble columns being identical or different.

12. The process of claim 11, wherein a temperature of 120° to 240° C. is employed.

13. The process of claim 1, wherein a pressure range of 0.05 to 15 bar is employed, in the case of a bubble column cascade, the pressures in the individual bubble column being identical or different.

14. The process of claim 13, wherein a pressure range of 0.08 to 13 bar is employed.

15. The process of claim 1, wherein in the case of a bubble column cascade, both the pressure and the temperature decrease from the first to the last bubble column.

16. The process of claim 1, wherein bubble columns having loose packings, arranged packings or perforated trays are used.

17. The process of claim 1, wherein a bubble column or a bubble column cascade is combined with one or more downstream residence time vessels.

18. The process of claim 1, wherein the organic carbonate (II) is used in a mixture with 0–5% by weight based on the weight of (II), of the underlying alcohol $R^3$—OH.

19. The process of claim 18, wherein the amount of the underlying alcohol in the mixture is 0.1–3% by weight.

20. The process of claim 1, wherein additionally to the starting materials, an inert solvent evaporating in the reaction mixture or an inert gas is fed in together with the carbonate of the formula (II) or separately therefrom at any desired position of the bubble column or bubble column cascade, which solvent or gas may or may not form an azeotrope with the product of the formula (IV).

* * * * *